(12) United States Patent
Caracciolo Torchiarolo et al.

(10) Patent No.: US 8,354,544 B2
(45) Date of Patent: Jan. 15, 2013

(54) PROCESS FOR THE PREPARATION OF 1-BENZYL-3-HYDROXYMETHYL-1H-INDAZOLE AND ITS DERIVATIVES AND REQUIRED MAGNESIUM INTERMEDIATES

(75) Inventors: Giuliano Caracciolo Torchiarolo, Aprilia (IT); Tommaso Iacoangeli, Rome (IT); Guido Furlotti, Rome (IT)

(73) Assignee: Aziende Chimiche Riunite Angelini Francesco A.C.R.A.F. S.p.A., Rome (IT)

( * ) Notice: Subject to any disclaimer, the term of this patent is extended or adjusted under 35 U.S.C. 154(b) by 0 days.

(21) Appl. No.: 13/377,588

(22) PCT Filed: Jul. 28, 2010

(86) PCT No.: PCT/EP2010/060937
§ 371 (c)(1),
(2), (4) Date: Feb. 29, 2012

(87) PCT Pub. No.: WO2011/015501
PCT Pub. Date: Feb. 10, 2011

(65) Prior Publication Data
US 2012/0184752 A1 Jul. 19, 2012

(30) Foreign Application Priority Data

Aug. 3, 2009 (EP) .................................. 09425314

(51) Int. Cl.
*C07D 231/56* (2006.01)
(52) U.S. Cl. .................................................. 548/362.5
(58) Field of Classification Search ................. 548/362.5
See application file for complete search history.

(56) References Cited

U.S. PATENT DOCUMENTS

| | | | |
|---|---|---|---|
| 3,262,850 | A | 7/1966 | Jones et al. |
| 4,999,367 | A | 3/1991 | Baiocchi et al. |
| 5,112,986 | A | 5/1992 | Baiocchi et al. |

FOREIGN PATENT DOCUMENTS

| | | |
|---|---|---|
| EP | 0 510 748 | 10/1992 |
| EP | 0 382 276 | 8/1995 |
| EP | 0 858 337 | 8/1998 |
| EP | 1 005 332 | 6/2000 |
| WO | 2008 061671 | 5/2008 |

OTHER PUBLICATIONS

Davis, R.D., et al., "Improved Method for the Synthesis of 2-Methyl-2-Aryloxypropanoic Acid Derivatives," Synthesis, vol. 12, pp. 1959-1962, (2004).
Cvetovich, R.J., et al., "An Efficient Synthesis of a dual PPAR a/y Agonist and the Formation of a Sterically Congested a-Aryloxyisobutyric Acid via a Bargellini Reaction," Journal of Organic Chemistry, vol. 70, pp. 8560-8563, (2005).
Gong, L.Z., et al., "Preparation of Highly Functionalized Heterocyclic Zinc Organometallics via a Li(acac)-Catalysis of the I/Zn-Exchange Reaction," Synlett, vol. 2, pp. 267-270, (2005).
Yang, X., et al., "Preparation and Reactions of Functionalized Organocopper Reagents," Synthesis, vol. 15, pp. 2618-2623, (2006).
Yang, X., et al., "Preparation and Acylation of Highly Functionalized Copper Derivatives of 3-Iodoindazoles Leading to Polyfunctional 3-Acylindazoles," Synlett, vol. 13, pp. 2303-2306, (2004).
Welch, W.M., et al., "A Novel Sythesis of 3-Substituted Indazole Derivatives," Synthesis, pp. 937-939, (Oct. 1992).
Tertov, B.A., "Zhurnal Organicheskoi Khimii," vol. 6, pp. 2140-2142, (1970).
Collot, V., et al., "Suzuki-Type Cross-Coupling Reaction of 3-Iodoindazoles with Aryl Boronic Acids: a General and Flexible Route to 3-Arylindazoles," Tetrahedron, vol. 55, pp. 6917-6922, (1999).

(Continued)

*Primary Examiner* — Rebecca Anderson
*Assistant Examiner* — Samantha Shterengarts
(74) *Attorney, Agent, or Firm* — Oblon, Spivak, McClelland, Maier & Neustadt, L.L.P.

(57) ABSTRACT

The present invention relates to the process for the preparation of 1-benzyl-3-hydroxymethyl-1H-indazole according to formula (II), to be used in a subsequent process for the preparation of 1-benzyl-3-hydroxymethyl-1H-indazole according to formula (I).

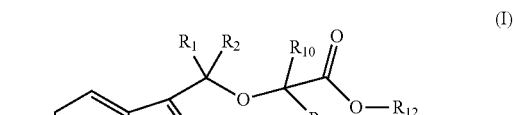

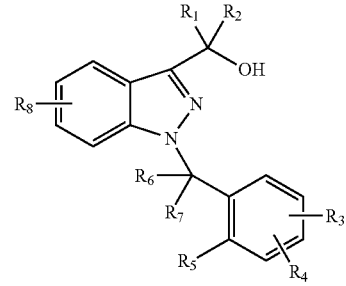

20 Claims, No Drawings

OTHER PUBLICATIONS

Boulton, B.E., "Kinetics, Stoichiometry and Mechanism in the Bromination of Aromatic Heterocycles. III Aqueous Bromination of Indazole," Australian Journal of Chemistry, vol. 27, pp. 2343-2347, (1974).

Silverman, G.S., "Common Methods of Grignard Reagent Preparation," Handbook of Grignard reagents, Chapter 2, pp. 9-21, (1996).

Ren, H., et al., "Preparation of cyclic alkenylmagnesium reagents via an iodine/magnesium exchange," Chemical Communications, pp. 543-545, (2005).

Smith, et al., "Attack by Hydrogen," Smith, March, March's Advanced Organic Chemistry, $5^{th}$ edition, Chapter 16, pp. 1197-1205, (1992).

"Group III Hydride-Donor Reagents," Carey, Sundberg, Advanced Organic Chemistry, $4^{th}$ edition, Chapter 5, pp. 262-290, (1929).

International Search Report Issued Sep. 23, 2010 in PCT/EP10/60937 Filed Jul. 28, 2010.

U.S. Appl. No. 13/381,137, filed Dec. 28, 2011, Caracciolo Torchiarolo, et al.

PROCESS FOR THE PREPARATION OF 1-BENZYL-3-HYDROXYMETHYL-1H-INDAZOLE AND ITS DERIVATIVES AND REQUIRED MAGNESIUM INTERMEDIATES

SCOPE OF THE INVENTION

This invention relates to a process for the preparation of 1-benzyl-3-hydroxymethyl-1H-indazole.

In particular, the present invention relates to the process for the preparation of 1-benzyl-3-hydroxymethyl-1H-indazole according to formula (II) below, to be used in a subsequent process for the preparation of 1-benzyl-3-hydroxymethyl-1H-indazole according to formula (I) below.

STATE OF THE ART

European patent EP-B-0 382 276 describes some 1-benzyl-3-hydroxymethyl-1 H-indazole derivatives of formula (A) having analgesic activity:

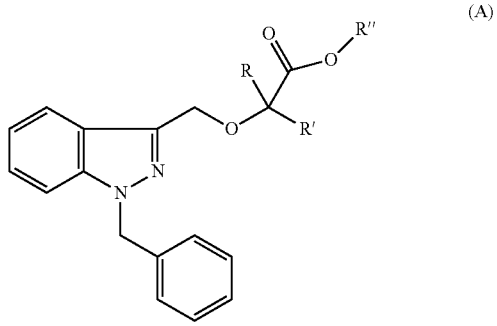

(A)

in which

R and R', which may be the same or different, are H or $C_{1-5}$ alkyl, and

R" is H or $C_{1-4}$ alkyl, possibly in the form of its salt with a pharmaceutically-acceptable organic or inorganic base when R" is H.

In turn, European patent EP-B-0 510 748 on the other hand describes the use of the same derivatives for the preparation of a pharmaceutical composition active in the treatment of autoimmune diseases.

In addition to this, document EP-B1-0 858 337 describes a pharmaceutical composition comprising a compound of formula (A) in which R=R'=$CH_3$ and R"=H, and an immunosuppressant.

European patent EP-B-1 005 332 describes the use of the same derivatives to prepare a pharmaceutical composition active in the treatment of conditions deriving from the production of MCP-1.

Finally international patent application WO 2008/061671 describes the use of a compound of formula (A) to reduce blood levels of triglycerides, cholesterol and glucose.

Various processes for the preparation of compounds of formula (A) are described in the abovementioned patent EP-B-0 382 276.

The processes described in patent EP-B-0 382 276 have as their key point the preparation of 1-benzyl-3-hydroxymethyl-1H-indazole, from which the compounds of formula (A) can be obtained via three different reaction routes.

The first reaction route provides for the conversion of 1-benzyl-3-hydroxymethyl-1H-indazole into the corresponding alcoholate which is then caused to react with X—CRR'—COOR", where X is a leaving group selected from the group comprising halogens, arylene-$SO_2$—O—, or alkylene-$SO_2$—O—, to yield the compounds of formula (A).

The second reaction route provides for the conversion of 1-benzyl-3-hydroxymethyl-1H-indazole into the corresponding 3-halogenomethyl derivative which is subsequently caused to react with an alcoholate of formula MeO—CRR'—COOR", where Me is an alkali metal, to yield the compounds of formula (A).

The third reaction route provides for the reaction of 1-benzyl-3-hydroxymethyl-1H-indazole with chloroform and a ketone of formula O=CRR' in the presence of an alkaline base such as sodium hydroxide to yield the compounds of formula (A) where R" is hydrogen.

Preparation of the key intermediate 1-benzyl-3-hydroxymethyl-1H-indazole by the processes described in patent EP-B-0 382 276 is carried out by reducing the corresponding 3-carboxylic acid with a suitable reducing agent, such as for example aluminium lithium hydride ($LAlH_4$).

BRIEF DESCRIPTION OF THE INVENTION

The Applicant has become aware that the processes of synthesis known in the art and described in the abovementioned patent EP-B-0 382 276 have a number of disadvantages.

Firstly, 1-benzyl-1(H)-indazol-3-carboxylic acid is not a product which can be easily obtained on the market, and is rather expensive. In particular there are few suppliers and the synthesis routes described in the literature provide for benzylation of the corresponding 1(H)-indazol-3-carboxylic acid, which is also expensive and not easy to obtain. In the second place, reduction of the 1-benzyl-1(H)-indazol-3-carboxylic acid to obtain 1-benzyl-3-hydroxymethyl-1H-indazole proceeds with high dilution factors.

Furthermore the second reaction route provides for the use of thionyl chloride to convert the 1-benzyl-3-hydroxymethyl-1H-indazole into the corresponding 3-chloromethyl derivative. The use of thionyl chloride, a highly toxic substance, gives rise to considerable safety and management problems in industrial processes.

Finally, the third reaction route (the Bargellini reaction) has shown industrial disadvantages in low yields (less than 50%), the production of carbon monoxide, a toxic and flammable gas, and the generation of significant exothermic phenomena which are difficult to manage industrially (Davis et al. *Synthesis*, 12, (2004), 1959-1962). Apart from this the Bargellini reaction finds better application in the synthesis of ethers from phenols and not from aliphatic alcohols (U.S. Pat. No. 3,262,850; Cvetovich et al., *J. Org. Chem.*, (2005), 70, 8560-8563).

The Applicant has therefore considered the problem of developing a new process for the preparation of 1-benzyl-3-hydroxymethyl-1H-indazole in order to obtain compounds of formula (A) which is capable of overcoming the abovementioned disadvantages. In particular the Applicant has extended the problem to the preparation of 1-benzyl-3-hydroxymethyl-1H-indazoles having the following formula (II).

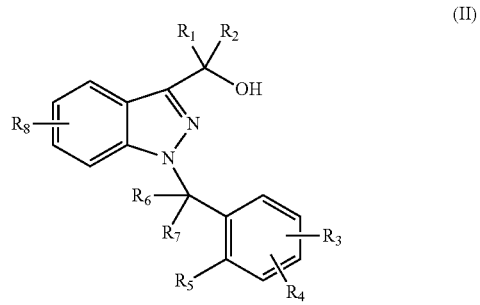

(II)

in order to obtain compounds having the following formula (I)

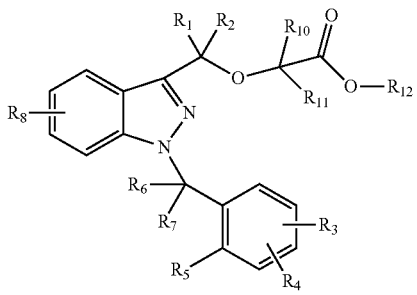

in which the substituents from $R_1$ to $R_{12}$ have the meanings indicated below in the detailed description and in the claims.

The Applicant has found a new process for the preparation of 1-benzyl-3-hydroxymethyl-1H-indazoles of formula (II) to obtain compounds of formula (I) which considerably improves on one hand industrial applicability, yields and the costs of the new process in comparison with the processes known hitherto, and on the other hand the quality of the compounds obtained using it.

The Applicant has surprisingly found that 1-benzyl-3-hydroxymethyl-1H-indazole, or its derivatives of formula (II), can easily be obtained by reacting a Grignard reagent having the formula (IV) described below with a suitable electrophilic compound such as, for example, aldehydes, ketones or amides, with subsequent reduction, if necessary, of the intermediate carbonyl compound.

In particular the Applicant has surprisingly found that the Grignard reagent of formula (IV) is easily obtained from 1-benzyl-3-halogeno-1H-indazole or its derivatives of formula (III) described below through a halogen/magnesium exchange reaction with Grignard reagents of the alkyl magnesium halide type, at low temperature.

The Applicant also believes that the Grignard reagents of formula (IV) are not known in the art.

In fact the only indazole organometallic derivatives known in the art, with the metal in the 3 position, are those with metals such as zinc (Knochel et al., *Synlett* 2005, 267) or copper (Knochel et al., *Synthesis* 2006, 15, 2618 and Knochel et al., *Synlett* 2004, 13, 2303-2306), while reactions degrading the indazole ring in an attempt to prepare the corresponding 3-organolithium compounds (Welch et al., *Synthesis*, 1992, 937) and 3-organosodium derivatives (Tertov et al., *Zhurnal Organicheskoi Khimii* 1970, 6; 2140) are known.

The said 1-benzyl-3-halogeno-1H-indazole derivatives of formula (III), which are widely known in the literature, can easily be obtained by halogenation of 1H-indazole in the 3 position with subsequent benzylation in the 1 position (Collot et al., *Tetrahedron*, 1999, 55, 6917; Coller et al., *Aust. J. Chem.* 1974, 27, 2343).

The Applicant has also surprisingly found that 1-benzyl-3-hydroxymethyl-1H-indazole, or its derivatives of formula (II), can be readily converted into the corresponding 3-halogenomethyl derivatives by mere treatment with hydrohalogen acids, and then to compounds of formula (I) by etherification with the appropriate hydroxycarboxylic acid or ester of formula (VI).

Alternatively the Applicant has also surprisingly found that 1-benzyl-3-hydroxymethyl-1H-indazole, or its derivatives of formula (II), can easily be converted into compounds of formula (I) by etherification with the appropriate α-halogenocarboxylic acid or ester of formula (VII) described below.

Thus a first aspect of the present invention relates to a process for the preparation of 1-benzyl-3-hydroxymethyl-1H-indazole and its derivatives represented by the following formula (II):

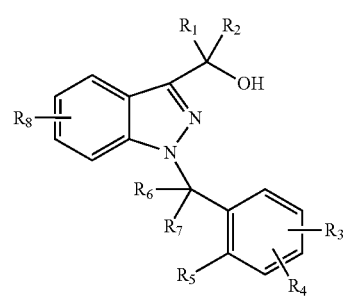

in which the substituents from $R_1$ to $R_8$ have the meanings indicated below in the detailed description and in the claims, in which a) a 1-benzyl-3-halogeno-1H-indazole of formula (III):

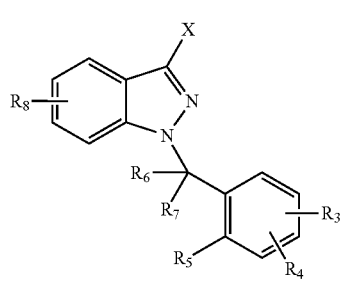

in which X is a halogen atom selected from iodine and bromine, preferably iodine,
is caused to react with an alkyl magnesium halide of formula RMgX' where R is an alkyl group having 1 to 6 carbon atoms and X' is a halogen atom selected from bromine and chlorine, preferably chlorine, to form intermediate compound (IV):

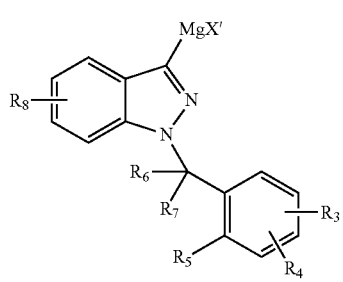

b) the said intermediate compound (IV) is caused to react with a carbonyl compound of formula $R_1$—CO—$R_2$ to form a compound of formula (II), or alternatively b') the said intermediate compound (IV) is caused to react with an amide of formula R'R"N—CO—$R_1$, where R' and R", which may be the same or different, are an alkyl group having 1 to 3 carbon atoms, to form an intermediate compound (VIII):

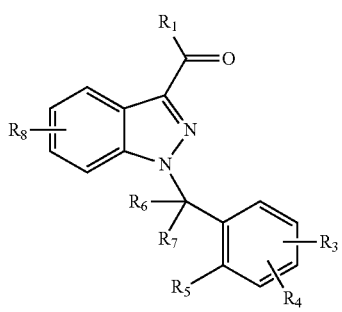

(VIII)

which is caused to react with a carbonyl group reducing agent to form a compound of formula (II).

The compound of formula (II) obtained with the process of the present invention can be used in a process for the preparation of 1-benzyl-3-hydroxymethyl-1H-indazole derivatives represented by the following formula (I):

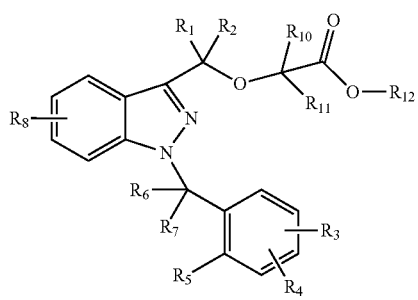

(I)

in which the substituents from $R_1$ to $R_{12}$ have the meanings indicated below in the detailed description and in the claims.

Finally, a second aspect of this invention relates to an intermediate compound represented by the following formula (IV):

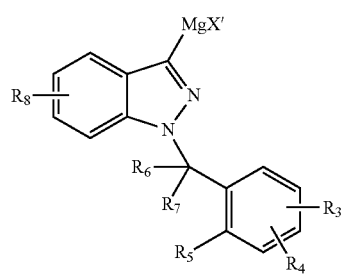

(IV)

in which X' is a halogen atom selected from bromine and chlorine, preferably chlorine, and the substituents from $R_3$ to $R_8$ have the meanings indicated below in the detailed description and in the claims.

DETAILED DESCRIPTION OF THE INVENTION

The first aspect of the present invention relates to a process for the preparation of 1-benzyl-3-hydroxymethyl-1H-indazole and its derivatives represented by the following formula (II):

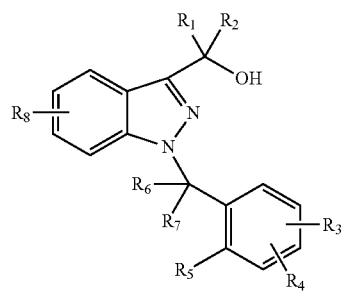

(II)

in which $R_1$ and $R_2$, which may be the same or different, are hydrogen or an alkyl group having from 1 to 6 carbon atoms, $R_3$, $R_4$ and $R_8$, which may be the same or different, may be hydrogen, an alkyl group having from 1 to 5 carbon atoms, an alkoxy group having from 1 to 3 carbon atoms, and a halogen atom, $R_5$ may be hydrogen, an alkyl group having from 1 to 5 carbon atoms, an alkoxy group having from 1 to 3 carbon atoms, a halogen atom, or together with one of $R_6$ and $R_7$ may form a ring having 5 or 6 carbon atoms, and $R_6$ and $R_7$, which may be the same or different, may be hydrogen, an alkyl group having from 1 to 5 carbon atoms, or one of $R_6$ and $R_7$ together with $R_5$ may form a ring having 5 or 6 carbon atoms.

The process for the preparation of 1-benzyl-3-hydroxymethyl-1H-indazole and its derivatives represented by the abovementioned formula (II) according to the invention provides that a) a 1-benzyl-3-halogeno-1H-indazole of formula (III):

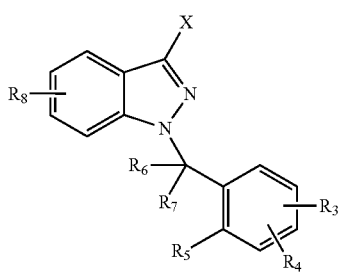

(III)

in which X is a halogen atom selected from iodine and bromine, preferably iodine, and $R_3$-$R_8$ have the abovementioned meanings, is caused to react with an alkyl magnesium halide of formula RMgX' where R is an alkyl group from 1 to 6 carbon atoms and X' is a halogen atom selected from bromine and chlorine, preferably chlorine, to form intermediate compound (IV):

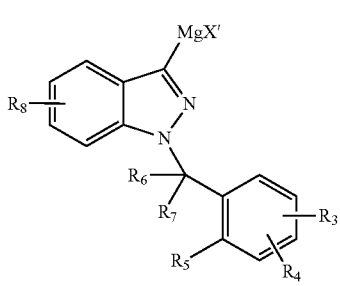

(IV)

b) the said intermediate compound (IV) is caused to react with a carbonyl compound of formula $R_1$—CO—$R_2$, where $R_1$ and $R_2$ have the abovementioned meanings, to form a compound of formula (II), or alternatively to b)

b') the said intermediate compound (IV) is caused to react with an amide of formula R'R''N—CO—$R_1$, where R' and R'', which may be the same or different, are an alkyl group having 1 to 3 carbon atoms and $R_1$ has the abovementioned meanings, to form an intermediate compound (VIII):

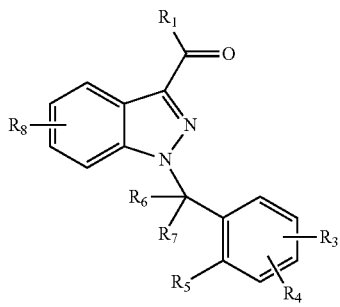

(VIII)

which is caused to react with a carbonyl group reducing agent to form a compound of formula (II).

Advantageously, stage a) is performed in the presence of a suitable solvent, such as for example tetrahydrofuran, 2-methyl-tetrahydrofuran, diethyl ether, dioxane, t-butyl-methyl ether, dibutyl ether, xylene, toluene, dichloromethane, chloroform, n-hexane, n-heptane and their mixtures and so on, preferably 2-methyl-tetrahydrofuran, tetrahydrofuran, toluene, xylene and their mixtures, and even more preferably 2-methyl-tetrahydrofuran.

The alkyl magnesium halide of formula RMgX' used in stage a) may be methylMgCl, ethylMgCl, n-propylMgCl, i-propylMgCl, n-butylMgCl, i-butylMgCl, sec-butylMgCl, t-butylMgCl, n-pentylMgCl, n-hexylMgCl, allylMgCl, cyclohexylMgCl, methylMgBr, ethylMgBr, n-propylMgBr, i-propylMgBr, n-butylMgBr, i-butylMgBr, sec-butylMgBr, t-butylMgBr, n-pentylMgBr, n-hexylMgBr, allylMgBr, cyclohexylMgBr, and preferably i-propylMgCl. These reagents may be obtained commercially or prepared according to methods extensively described in the literature (Silverman et al., *Handbook of Grignard reagents*, Chapter 2, CRC Press).

Advantageously, the exchange reaction in stage a) may be catalysed by the addition of lithium salts, for example LiCl, as described in the literature (Knochel et al., *Chem. Commun.*, 2005, 543).

Advantageously, stage a) is carried out at a temperature of between −30° C. and +30° C., preferably at a temperature of between −20° C. and −10° C.

Advantageously, stage a) is carried out using a molar ratio between the alkyl magnesium halide of formula RMgX' and the 1-benzyl-3-halogeno-1H-indazole of formula (III) of between 1 and 4, preferably between 1.5 and 4.

Advantageously, stage b) is carried out in the presence of a suitable solvent, such as for example tetrahydrofuran, 2-methyl-tetrahydrofuran, diethyl ether, dioxane, t-butylmethyl ether, dibutyl ether, xylene, toluene, dichloromethane, chloroform, n-hexane, n-heptane and their mixtures, and so on, preferably 2-methyl-tetrahydrofuran, tetrahydrofuran, toluene, xylene and their mixtures, but preferably 2-methyl-tetrahydrofuran.

Advantageously, stage b) is carried out using a carbonyl compound selected from the group of aldehydes, such as for example formaldehyde, acetaldehyde, propanal, butanal, pentanal, hexanal, and the like, and ketones such as for example acetone, ethylmethyl ketone, isobutylmethyl ketone, and so on. Formaldehyde is preferably used, and in particular polymers such as suitably depolymerised paraformaldehyde or trioxane are used as a source of formaldehyde.

Advantageously, stage b) is carried out using a molar ratio between the 1-benzyl-3-halogeno-1H-indazole of formula (III) and the carbonyl compound of formula $R_1$—CO—$R_2$ of between 1 and 6.

Advantageously, stage b) is carried out at a temperature of between −30° C. and +30° C., preferably at a temperature of between −10° C. and 0° C.

Advantageously, stage b') is carried out using an alkyl amide selected from the group comprising N,N-dimethylformamide, N,N-diethylformamide, N,N-di-n-propylformamide, N,N-dimethylacetamide, N,N-diethylacetamide, N,N-di-n-propylacetamide, N,N-dimethylpropionamide, N,N-diethylpropionamide, N,N-di-n-propylpropionamide, preferably N,N-dimethylformamide.

Advantageously, stage b') is carried out at a temperature of between −30° C. and +30° C., preferably at a temperature of between −10° C. and 0° C.

In particular, stage b') is carried out using a molar ratio between the 1-benzyl-3-halogeno-1H-indazole of formula (III) and the amide of formula R'R''N—CO—$R_1$ of between 1 and 4.

Advantageously, the carbonyl group reducing agent used in stage b') is selected from the group comprising hydrides, such as for example $NaBH_4$, $KBH_4$, $LiBH_4$, $Zn(BH_4)_2$, $Ca(BH_4)_2$, $NaAlH_4$, $LiAlH_4$, $Et_3SiH$, $Bu_3SnH$, $i-Bu_2AlH$, 70% $NaAlH_2(OCH_2CH_2OCH_3)_2$ in toluene, and derivatives. The carbonyl group reducing agent is preferably 70% $NaAlH_2(OCH_2CH_2OCH_3)_2$ in toluene. Carbonyl group reducing agents are extensively reported in the literature (described, for example, in Smith, March, *March's Advanced Organic Chemistry*, 5th ed., pages 1197-1205, John Wiley & Sons, Inc. and Carey, Sundberg, *Advanced Organic Chemistry*, 4th ed., pages 262-290).

Advantageously, the reduction in stage b') is carried out in the presence of a suitable solvent such as for example tetrahydrofuran, 2-methyl-tetrahydrofuran, diethyl ether, dioxane, t-butylmethyl ether, dibutyl ether, xylene, toluene, dichloromethane, chloroform, n-hexane, n-heptane, methanol, ethanol, n-propanol, i-propanol, diglyme (bis-(2-methoxyethyl)ether), pyridine, dimethylsulphoxide (DMSO), acetic acid, their mixtures and so on, preferably toluene, xylene, tetrahydrofuran, 2-methyl-tetrahydrofuran and their mixtures.

Advantageously the reduction in stage b') is carried out at a temperature of between 10° and 100° C., preferably at a temperature of between 20° C. and 60° C.

In particular, reduction of the carbonyl group in stage b') is carried out using a number of equivalents of hydride of between 1 and 3, preferably 2.

Advantageously, the $R_1$-$R_8$ groups in formulae (II), (III), (IV) and (VIII) described above may have the following meanings.

Preferably, $R_1$ and $R_2$, which may be the same or different, are represented by a hydrogen atom, or an alkyl group having from 1 to 3 carbon atoms.

Preferably, $R_3$, $R_4$ and $R_8$, which may be the same or different, may be hydrogen, a methyl group, an ethyl group, a methoxy group, an ethoxy group, a chlorine atom and a fluorine atom.

Advantageously, $R_5$ may be hydrogen, a methyl group, an ethyl group, a methoxy group, an ethoxy group, a chlorine atom and a fluorine atom, or together with one of $R_6$ and $R_7$ may form a ring having 6 carbon atoms.

Preferably, $R_6$ and $R_7$, which may be the same or different, may be hydrogen, a methyl group, an ethyl group, or one of $R_6$ and $R_7$ together with $R_5$ may form a ring having 6 carbon atoms.

Advantageously, the compound of formula (II) obtained with the process of the present invention is used in a process for the preparation of 1-benzyl-3-hydroxymethyl-1H-indazole derivatives represented by the following formula (I):

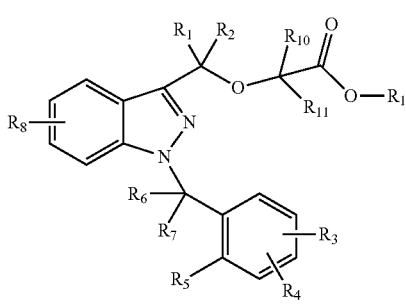

(I)

in which
$R_1$-$R_8$ have the meanings in formula (II) above,
$R_{10}$ and $R_{11}$, which may be the same or different, are hydrogen or an alkyl group having from 1 to 5 carbon atoms, and
$R_{12}$ is hydrogen or an alkyl group having from 1 to 4 carbon atoms.

Preferably, the process for preparation of the 1-benzyl-3-hydroxymethyl-1H-indazole derivatives shown in the abovementioned formula (I) provides that a) the 1-benzyl-3-hydroxymethyl-1H-indazole or a derivative thereof represented by the following formula (II):

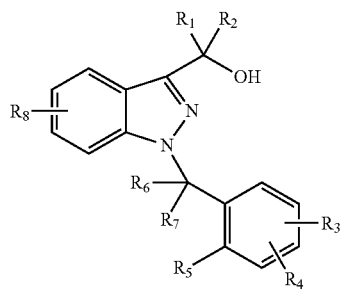

(II)

in which $R_1$-$R_8$ have the abovementioned meanings,
is caused to react with a hydrohalogen acid of formula HX″, where X″ is a halogen atom selected from the group consisting in chlorine, bromine and iodine, preferably chlorine, to form 1-benzyl-3-halogenomethyl-1H-indazole or a derivative thereof represented by the following formula (V):

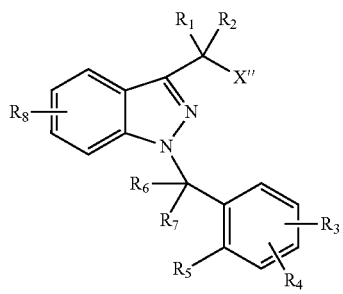

(V)

in which $R_1$-$R_8$ and X″ have the abovementioned meanings, b) the 1-benzyl-3-halogenomethyl-1H-indazole or a derivative thereof represented by the abovementioned formula (V) are caused to react in the presence of a strong base with a compound represented by the following formula (VI):

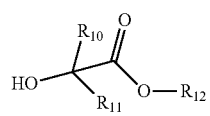

(VI)

in which $R_{10}$, $R_{11}$, which may be the same or different, and $R_{12}$ have the abovementioned meanings, to form the 1-benzyl-3-hydroxymethyl-1H-indazole derivatives represented by the above formula (I).

Alternatively, the process for preparation of the 1-benzyl-3-hydroxymethyl-1H-indazole derivatives shown in the abovementioned formula (I) provides that a') the 1-benzyl-3-hydroxymethyl-1H-indazole or a derivative thereof represented by the abovementioned formula (II) is caused to react in the presence of a strong base with a compound represented by the following formula (VII)

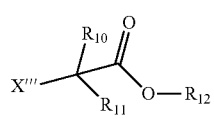

(VII)

in which $R_{10}$, $R_{11}$, which may be the same or different, and $R_{12}$ have the abovementioned meanings and X‴ is a halogen atom selected from the group consisting in chlorine, bromine and iodine, preferably bromine, to form the 1-benzyl-3-hydroxymethyl-1H-indazole derivatives represented by the abovementioned formula (I).

Preferably the abovementioned process for the preparation of the 1-benzyl-3-hydroxymethyl-1H-indazole derivatives represented by formula (I) may comprise formation of the salt of the carboxyl group represented by —COOR$_{12}$ by treatment with a pharmaceutically acceptable organic or inorganic base. This treatment may be carried out directly on the corresponding acid when $R_{12}$ is hydrogen, or following the reaction of hydrolysing the ester when $R_{12}$ is an alkyl group from 1 to 4 carbon atoms.

Advantageously, stage a) is carried out in aqueous solution or in organic solvent. The hydrohalogen acid of formula HX″ used is concentrated or dilute hydrochloric acid, hydrobromic acid or hydroiodic acid, preferably hydrochloric acid in a concentration such as to have a molar ratio between the acid and the compound of formula (II) of between 1 and 20, preferably between 1 and 5, and even more preferably approximately 3.

Advantageously, stage a) is carried out at a temperature of between 25° C. and 100° C., preferably at a temperature of between 60° C. and 90° C.

The organic solvent preferably used in stage a) is selected from the group comprising toluene, xylene, acetic acid, dioxane, dibutylether, 2-methyl-tetrahydrofuran.

Advantageously, stage b) is carried out in aprotic solvents, such as for example tetrahydrofuran, dioxane, N,N-dimethylformamide, toluene, N-methylpyrrolidone, dimethylsulphoxide, hexamethylphosphoramide, acetone, isobutylmethyl ketone, methylethyl ketone or their mixtures, preferably toluene or N,N-dimethylformamide and their mixtures.

The strong base used in stage b) is preferably selected from the group comprising sodium hydride, metallic sodium, metallic potassium, butyl lithium, lithium-diisopropyl amide, sodium amide, potassium hydride, preferably sodium hydride.

Advantageously, stage b) is carried out using an α-hydroxy acid selected from the group comprising hydroxyacetic acid, lactic acid, α-hydroxyisobutyric acid, α-hydroxybutyric acid, 2-ethyl-2-hydroxybutyric acid, 2-hydroxyisovaleric acid, 2-hydroxy-3,3-dimethylbutyric acid, 2-hydroxyisocaproic acid, preferably α-hydroxyisobutyric acid.

Advantageously, stage b) is carried out using an α-hydroxyester selected from the group comprising methyl glycolate, ethyl glycolate, butyl glycolate, methyl lactate, ethyl lactate, butyl lactate, t-butyl lactate, isopropyl lactate, isobutyl lactate, methyl-2-hydroxyisobutyrate, ethyl-2-hydroxyisobutyrate, ethyl-2-hydroxyvalerate, t-butyl-2-hydroxybutyrate, preferably ethyl-2-hydroxyisobutyrate.

Preferably, the molar ratio between the 1-benzyl-3-halomethyl-1H-indazole of formula (V) and the α-hydroxy acid or ester of formula (VI) is between 1 and 2, preferably approximately 1.2.

In particular, the molar ratio between the α-hydroxy acid of formula (VI) and the strong base is between 1 and 3, preferably approximately 2. Similarly the molar ratio between the α-hydroxy ester of formula (VI) and the strong base is between 1 and 1.5, preferably approximately 1.

Advantageously, the compound represented by formula (VII) used in stage a') is an α-halogen acid selected from the group comprising bromoacetic acid, 2-bromopropionic acid, 2-bromobutyric acid, 2-bromoisobutyric acid, 2-bromo-2-butylpropionic acid, 2-bromovaleric acid, α-bromoisovaleric acid, preferably α-bromo isobutyric acid.

Preferably, stage a') is carried out with a molar ratio between the 1-benzyl-3-hydroxymethyl-1H-indazole of formula (II) and the α-halogeno acid or ester of formula (VII) of between 1 and 3, advantageously approximately 3.

Advantageously, stage a') is carried out in aprotic solvents such as for example tetrahydrofuran, dioxane, N,N-dimethylformamide, toluene, N-methylpyrrolidone, dimethylsulphoxide, hexamethylphosphoramide, acetone, isobutylmethyl ketone, methylethyl ketone or their mixtures, preferably methylethyl ketone.

The strong base used in stage a') is preferably selected from the group comprising sodium hydride, potassium hydride, metallic sodium, metallic potassium, sodium hydroxide, potassium hydroxide, preferably sodium hydroxide.

The molar ratio between the 1-benzyl-3-hydroxymethyl-1H-indazole of formula (II) and the strong base is preferably between 1 and 15, and more preferably approximately 9.

Advantageously, stage a') is carried out at a temperature of between 25° C. and 100° C., preferably at a temperature of between 50° C. and 70° C.

Advantageously, the groups $R_1$-$R_{12}$ in formulae (I), (II), (V), (VI) and (VII) described above may have the following meanings.

Preferably $R_1$ and $R_2$, which may be the same or different, are represented by a hydrogen atom, or an alkyl group having from 1 to 3 carbon atoms.

Preferably, $R_3$, $R_4$ and $R_8$, which may be the same or different, may be hydrogen, a methyl group, an ethyl group, a methoxy group, an ethoxy group, a chlorine atom and a fluorine atom.

Advantageously, $R_5$ may be hydrogen, a methyl group, an ethyl group, a methoxy group, an ethoxy group, a chlorine atom and a fluorine atom, or together with one of $R_6$ and $R_7$ may form a ring having 6 carbon atoms.

Preferably, $R_6$ and $R_7$, which may be the same or different, may be hydrogen, a methyl group, an ethyl group, or one of $R_6$ and $R_7$ together with $R_5$ may form a ring having 6 carbon atoms.

Preferably, $R_{10}$ and $R_{11}$, which may be the same or different, are hydrogen or an alkyl group having 1 to 3 carbon atoms, and $R_{12}$ is hydrogen or an alkyl group having 1 to 3 carbon atoms.

The following examples are intended to illustrate this invention without however restricting it in any way.

EXPERIMENTAL PART

The compounds 3-iodo-1H-indazole and 1-benzyl-3-iodo-1H-indazole were prepared according to the procedure reported by Collot et al. (*Tetrahedron*, 55, 6917, 1999). The compound 3-bromo-1H-indazole was prepared using the procedure reported by Coller et al. (*Aust. J. Chem.* 1974, 27, 2343).

Example 1

Preparation of 1-benzyl-3-bromoindazole 3-bromo-1H-indazole (90.4 g, 0.459 mol, 1.0 eq.) and toluene (450 mL) were placed in a 1 litre flask fitted with a mechanical stirrer under an atmosphere of nitrogen. Then potassium t-butoxide (t-BuOK, 54.2 g, 0.483 mol, 1.05 eq.) was added at room temperature over about half an hour and benzyl bromide (86.3 g, 0.505 mol, 1.1 eq.) was added over approximately 1.5 hours. The mixture was left stirred at the same temperature until the reaction was complete (checked by TLC, approximately 3 hours). Then 0.1 M HCl (45 mL) and water (90 mL) were added and the resulting phases were separated. The organic phase was washed with water, and the solvent was evaporated off at reduced pressure in order to obtain a red oily residue. The product was then precipitated through the addition of n-heptane, filtered and dried under vacuum at room temperature. Yield: 65.9 g of beige solid (yield 50%).

$^1$H NMR (300 MHz, DMSO-$d_6$) δ (ppm) 5.67 (s, 2H), 7.29 (m, 6H), 7.50 (ddd, 1H, J=8.6 Hz, 6.9 Hz, 1.0 Hz), 7.60 (dd, 1H, J=8.2 Hz, 0.7 Hz), 7.80 (dd, 1H, J=8.6 Hz, 0.7 Hz).

$^{13}$C NMR (300 MHz, DMSO-$d_6$) δ (ppm) 52.2, 110.4, 119.5, 121.7, 122.9, 127.4, 127.4, 127.6, 127.7, 128.6, 128.6, 129.6, 136.9, 140.5.

Example 2

Preparation of 1-benzyl-3-hydroxymethyl-1H-indazole

A solution of i-propylmagnesium chloride (i-PrMgCl) in 2-methyltetrahydrofuran (Me-THF) was prepared in a suitably thoroughly dried flask maintained under an atmosphere of nitrogen from magnesium metal (Mg, 10.91 g, 0.4489 mol, 1.5 eq.) activated with iodine crystals and a solution of isopropyl chloride (i-PrCl, 41.0 mL, 0.4489 mol, 1.5 eq.) in anhydrous Me-THF (185 mL). After cooling to approximately −10° C. a solution of 1-benzyl-3-iodo-1H-indazole (100 g, 0.2993 mol, 1.0 eq.) in anhydrous Me-THF (120 mL) was added over 1 hour keeping the temperature constant. The reaction mixture was kept stirred for a further hour to complete the halogen/magnesium exchange, and a yellow suspension was obtained. Gaseous formaldehyde (generated by heating a suspension of 54 g of paraformaldehyde in 150 mL of xylene at approximately 115° C.) was passed over this for approximately two hours at a temperature of below 0° C. When the reaction was complete, dilute H₃PO₄ was added and the excess of re-polymerised paraformaldehyde was removed by filtration. The phases were separated and the organic phase was then washed with a dilute solution of NaHCO₃ and then concentrated. The product, precipitated out by the addition of n-hexane, was collected by filtration and dried. Yield: 56.8 g of white solid (79.6%).

mp: 85-86° C.

$^1$H NMR (300 MHz, DMSO-d$_6$) δ (ppm) 4.79 (d, 2H, J=5.8 Hz), 5.27 (t, 1H, J=5.8 Hz), 5.6 (s, 2H), 7.12 (t, 1H, J=7.5 Hz), 7.28 (m, 5H), 7.36 (t, 1H, J=7.2 Hz), 7.64 (d, 1H, J=8.5 Hz), 7.86 (d, 1H, J=8.2 Hz).

$^{13}$C NMR (300 MHz, DMSO-d$_6$) δ (ppm) 51.6, 56.6, 109.6, 120.0, 120.9, 122.2, 126.2, 127.3, 127.3, 127.4, 128.5, 128.5, 137.7, 140.3, 145.2.

Example 3

Preparation of 1-benzyl-3-hydroxymethyl-1H-indazole

A solution of 2M i-PrMgCl in THF (69 mL, 138 mmol, 4.0 eq.) was added to a suitably thoroughly dried flask maintained under a nitrogen atmosphere. The solution was cooled to approximately −10° C. A solution of 1-benzyl-3-bromo-1H-indazole (10 g, 34.8 mmol, 1.0 eq.) in anhydrous THF (40 mL) was added over approximately one hour keeping the temperature constant. The reaction mixture was kept stirred for at least 6 hours, and a yellow suspension was obtained. Gaseous formaldehyde (generated by heating a suspension of 16.7 g of paraformaldehyde in 60 mL of xylene at approximately 115° C.) was passed over this for approximately two hours at a temperature of below 0° C. When the reaction was complete, dilute H₃PO₄ was added and the excess of re-polymerised paraformaldehyde was removed by filtration. Me-THF (60 mL) was added to the mixture and the phases were separated. The organic phase was washed with a dilute solution of NaHCO₃. After concentration of the organic phase an oily residue containing the product was obtained. Subsequent purification of the crude product by silica gel chromatography yielded 2.8 g of white solid (yield: 34%).

mp: 85-86° C.

$^1$H NMR (300 MHz, DMSO-d$_6$) δ (ppm) 4.79 (d, 2H, J=5.8 Hz), 5.27 (t, 1H, J=5.8 Hz), 5.6 (s, 2H), 7.12 (t, 1H, J=7.5 Hz), 7.28 (m, 5H), 7.36 (t, 1H, J=7.2 Hz), 7.64 (d, 1H, J=8.5 Hz), 7.86 (d, 1H, J=8.2 Hz).

$^{13}$C NMR (300 MHz, DMSO-d$_6$) δ (ppm) 51.6, 56.6, 109.6, 120.0, 120.9, 122.2, 126.2, 127.3, 127.3, 127.4, 128.5, 128.5, 137.7, 140.3, 145.2.

Example 4

Preparation of 1-benzyl-3-chloromethyl-1H-indazole 1-benzyl-3-hydroxymethyl-1H-indazole (400 g, 1.7 mol, 1 eq.), toluene (1.6 L) and concentrated HCl (422 mL, 5.1 mol, 3.0 eq.) were added to a three-necked flask fitted with a mechanical stirrer and reflux condenser.

The reaction mixture was heated to approximately 90° C. and kept stirred until the reaction was complete (checked by TLC, approximately two hours). After cooling to room temperature NaCl was added (approximately 10 g), the phases were separated, and the aqueous phase was discharged. The organic phase was washed with a saturated solution of NaHCO₃ (approximately 100 mL) and then concentrated.

The product, precipitated out by the addition of n-hexane (approximately 500 mL), was filtered and dried. Yield: 398.2 g of white solid (91%).

mp: 89-91° C.

$^1$H NMR (300 MHz, DMSO-d$_6$) δ (ppm) 5.14 (s, 2H), 5.65 (s, 2H), 7.27 (m, 6H), 7.43 (m, 1H), 7.12 (d, 1H, J=8.5 Hz), 7.88 (d, 1H, J=8.2 Hz)

$^{13}$C NMR (300 MHz, DMSO-d$_6$) δ (ppm) 38.2, 51.8, 110.2, 120.1, 120.9, 121.7, 126.7, 127.3, 127.3, 127.5, 128.5, 128.5, 137.2, 140.4, 140.6.

Example 5

Preparation of 2-[(1-benzyl-1H-indazol-3-yl)methoxy]-2-methylpropanoic acid

Ethyl-2-hydroxyisobutyrate (18.5 g, 140 mmol, 1.2 eq.), toluene (100 mL) and DMF (20 mL) were placed in a three-necked flask fitted with a mechanical stirrer and a reflux condenser under an inert atmosphere. A dispersion of 60% NaH (5.6 g, 140 mmol, 1.2 eq.) was added to the mixture in portions over a period of approximately 1.5 hours. A solution of 1-benzyl-3-chloromethyl-1H-indazole (30 g, 117 mmol, 1 eq.) in toluene (90 mL) and DMF (60 mL) was then added dropwise. The reaction mixture was heated to approximately 90° C. and kept at that temperature until the reaction was complete (checked by TLC, approximately 10 hours). After cooling to room temperature the mixture was washed with acidified water and water. The organic phase was concentrated under reduced pressure and the oily residue obtained was treated with 10 M NaOH (36 mL) at reflux temperature for at least 3 hours. The product, which was precipitated out by the addition of concentrated HCl, was filtered and dried. Yield: 32.3 g of white solid (85%).

mp: 133-134° C.

Elemental Analysis:

Calculated: C (70.35); H, (6.21); N (8.64),

Found: C, (70.15); H, (6.17); N, (8.63).

$^1$H NMR (300 MHz, DMSO-d$_6$) δ (ppm) 1.44 (s, 6H), 4.76 (s, 2H), 5.60 (s, 2H), 7.14 (t, 1H, J=7.6 Hz), 7.20-7.34 (m, 5H), 7.37 (ddd, 1H, J=8.3 Hz, 7.0 Hz, 1.1 Hz), 7.66 (d, 1H, J=8.4 Hz), 7.94 (d, 1H, J=8.1 Hz), 12.77 (s, 1H).

$^{13}$C NMR (300 MHz, DMSO-d$_6$) δ (ppm) 24.48, 24.48, 51.63, 59.65, 76.93, 109.69, 120.22, 121.06, 122.62, 126.28, 127.36, 127.36, 127.44, 128.46, 128.46, 137.49, 140.31, 141.97, 175.46.

Example 6

Preparation of 1-benzyl-1H-indazol-3-carbaldehyde

A solution of i-PrMgCl in THF was prepared in a suitably thoroughly dried flask maintained under a nitrogen atmosphere from magnesium metal (Mg, 164 mg, 6.75 mmol, 1.5 eq.) activated with iodine crystals and a solution of i-PrCl (0.62 mL, 6.75 mmol, 1.5 eq.) in anhydrous THF (2.8 mL).

After cooling to approximately −10° C. a solution of 1-benzyl-3-iodo-1H-indazole (1.5 g, 4.5 mmol, 1.0 eq.) in anhydrous THF (5 mL) was added to the reaction mixture over one hour keeping the temperature constant. The reaction mixture was kept stirred for a further hour to complete the halogen/magnesium exchange, yielding a yellow suspension. While stirring, dimethylformamide (DMF) (1.4 mL, 18 mmol, 4 eq.) was added to the suspension over one hour at a temperature below 0° C. and the reaction mixture was kept stirred at the same temperature until the reaction was complete (checked by TLC).

Dilute $H_3PO_4$ and toluene were added to the reaction mixture and the phases were separated. The organic phase was washed with a solution of dilute $NaHCO_3$. After the organic phase had been concentrated, the product, precipitated out by the addition of n-hexane, was filtered and dried. Yield: 1.0 g of yellowish solid (94%).

$^1$H NMR (300 MHz, DMSO-$d_6$) δ (ppm) 5.84 (s, 2H), 7.32 (m, 5H), 7.39 (ddd, 1H, J=8.1 Hz, 7.0 Hz, 1.0 Hz), 7.53 (ddd, 1H, J=8.4 Hz, 7.0 Hz, 1.2 Hz) 7.90 (dt, 1H, J=8.5 Hz, 1.0 Hz), 8.16 (dt, 1H, J=8.1 Hz, 1.2 Hz), 10.19 (s, 1H).

$^{13}$C NMR (300 MHz, DMSO-$d_6$) δ (ppm) 52.9, 111.0, 121.0, 121.2, 124.2, 127.5, 127.6, 127.6, 127.9, 128.6, 128.6, 136.2, 140.7, 142.4, 186.8.

Example 7

Preparation of 1-benzyl-3-hydroxymethyl-1H-indazole 1-benzyl-1H-indazol-3-carbaldehyde (2.36 g, 10 mmol, 1 eq.) and toluene (12 mL) were placed in a thoroughly dried 100 mL flask fitted with a magnetic stirrer and inerted with nitrogen. A 70% solution of sodium dihydro-bis(2-methoxyethoxy)aluminate in toluene (2.8 mL, 10 mmol, 2 eq.) was then slowly added to the solution at room temperature. Once the reaction was complete (after approximately 15 minutes), 2 M HCl (10 mL), $H_2O$ (10 mL) and toluene (15 mL) were added. The phases were separated and the aqueous phase was extracted twice with toluene. The pooled organic phases were washed with water and concentrated. The product was then precipitated out by adding n-hexane, filtered and dried. Yield: 1.95 g of white solid (82.0%).

mp: 85-86° C.

$^1$H NMR (300 MHz, DMSO-$d_6$) δ (ppm) 4.79 (d, 2H, J=5.8 Hz), 5.27 (t, 1H, J=5.8 Hz), 5.6 (s, 2H), 7.12 (t, 1H, J=7.5 Hz), 7.28 (m, 5H) 7.36 (t, 1H, J=7.2 Hz), 7.64 (d, 1H, J=8.5 Hz), 7.86 (d, 1H, J=8.2 Hz).

$^{13}$C NMR (300 MHz, DMSO-$d_6$) δ (ppm) 51.6, 56.6, 109.6, 120.0, 120.9, 122.2, 126.2, 127.3, 127.3, 127.4, 128.5, 128.5, 137.7, 140.3, 145.2.

The invention claimed is:

1. A process for the preparation of 1-benzyl-3-hydroxymethyl-1H-indazole represented by the following formula (II):

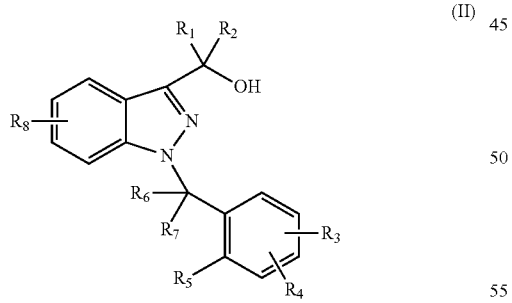

(II)

in which
$R_1$ and $R_2$, which may be the same or different, are hydrogen or an alkyl group having from 1 to 6 carbon atoms,
$R_3$, $R_4$ and $R_8$, which may be the same or different, may be hydrogen, an alkyl group having 1 to 5 carbon atoms, an alkoxy group having 1 to 3 carbon atoms, and a halogen atom,
$R_5$ may be hydrogen, an alkyl group having from 1 to 5 carbon atoms, an alkoxy group having from 1 to 3 carbon atoms, a halogen atom, or together with $R_6$ and $R_7$ may form a ring having 5 or 6 carbon atoms, and $R_6$ and $R_7$, which may be the same or different, may be hydrogen, an alkyl group having 1 to 5 carbon atoms, or one of $R_6$ and $R_7$ together with $R_5$ may form a ring having 5 or 6 carbon atoms,
in which
a) a 1-benzyl-3-halogeno-1H-indazole of formula (III):

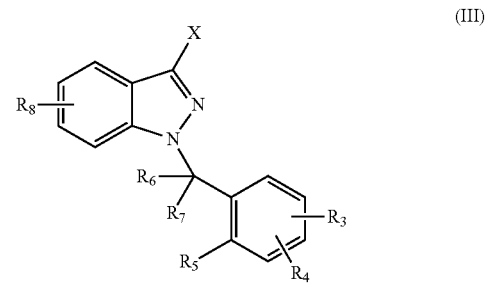

(III)

in which X is a halogen atom selected from iodine and bromine,
is caused to react with an alkyl magnesium halide of formula RMgX' where R is an alkyl group having 1 to 6 carbon atoms and X' is a halogen atom selected from bromine and chlorine, preferably chlorine, to form intermediate compound (IV):

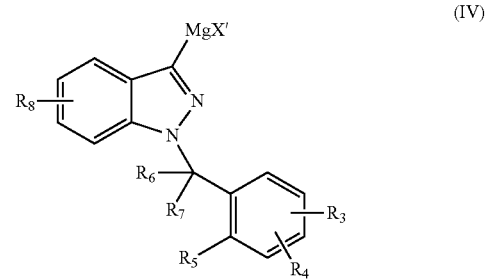

(IV)

b) the said intermediate compound (IV) is caused to react with a carbonyl compound of formula $R_1$—CO—$R_2$ to form a compound of formula (II), or alternatively to b)
b') the said intermediate compound (IV) is caused to react with an amide of formula R'R"N—CO—$R_1$, where R' and R", which may be the same or different, are an alkyl group having 1 to 3 carbon atoms, to form an intermediate compound (VIII):

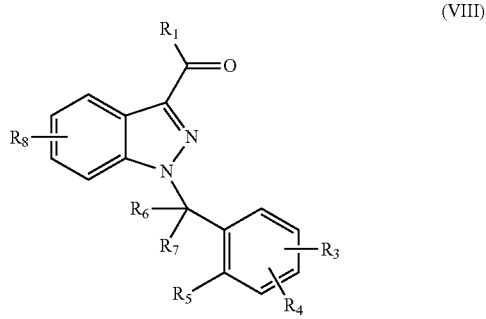

(VIII)

which is caused to react with a carbonyl group reducing agent to form a compound of formula (II).

2. The process for the preparation of 1-benzyl-3-hydroxymethyl-1H-indazole represented by formula (II)

according to claim 1, in which the said stages a) and b) are carried out in the presence of a solvent selected from the group consisting of tetrahydrofuran, 2-methyl-tetrahydrofuran, diethyl ether, dioxane, t-butyl-methyl ether, dibutyl ether, xylene, toluene, dichloromethane, chloroform, n-hexane, n-heptane and their mixtures, and the said stage b') is carried out in the presence of a solvent selected from the group consisting of tetrahydrofuran, 2-methyltetrahydrofuran, diethyl ether, dioxane, t-butylmethyl ether, dibutyl ether, xylene, toluene, dichloromethane, chloroform, n-hexane, n-heptane, methanol, ethanol, n-propanol, i-propanol, diglyme, pyridine, DMSO, acetic acid and their mixtures.

3. The process for the preparation of 1-benzyl-3-hydroxymethyl-1H-indazole represented by formula (II) according to claim 1, in which the said alkyl magnesium halide of formula RMgX' is selected from the group consisting of methylMgCl, ethylMgCl, n-propylMgCl, i-propylMgCl, n-butylMgCl, i-butylMgCl, sec-butylMgCl, t-butylMgCl, n-pentylMgCl, n-hexylMgCl, allylMgCl, cyclohexylMgCl, methylMgBr, ethylMgBr, n-propylMgBr, i-propylMgBr, n-butylMgBr, i-butylMgBr, sec-butylMgBr, t-butylMgBr, n-pentylMgBr, n-hexylMgBr, allylMgBr and cyclohexylMgBr, preferably i-propylMgCl.

4. The process for the preparation of 1-benzyl-3-hydroxymethyl-1H-indazole represented by formula (II) according to claim 1, in which the said stage a) is carried out using a molar ratio between the alkyl magnesium halide of formula RMgX' and the 1-benzyl-3-halogeno-1H-indazole of formula (III) of between 1 and 4.

5. The process for the preparation of 1-benzyl-3-hydroxymethyl-1H-indazole represented by formula (II) according to claim 1, in which the said carbonyl compound of formula $R_1$—CO—$R_2$ is selected from the group consisting of aldehydes and ketones.

6. The process for the preparation of 1-benzyl-3-hydroxymethyl-1H-indazole represented by formula (II) according to claim 1, in which the said carbonyl compound of formula $R_1$—CO—$R_2$ is selected from the group consisting of formaldehyde, acetaldehyde, propanal, butanal, pentanal, hexanal, acetone, methylethyl ketone and isobutylmethyl ketone, preferably formaldehyde.

7. The process for the preparation of 1-benzyl-3-hydroxymethyl-1H-indazole represented by formula (II) according to claim 1, in which the said stage b) is carried out using a molar ratio between the 1-benzyl-3-halogeno-1H-indazole of formula (III) and the carbonyl compound of formula $R_1$—CO—$R_2$ of between 1 and 6.

8. The process for the preparation of 1-benzyl-3-hydroxymethyl-1H-indazole represented by formula (II) according to claim 1, in which the said amide of formula R'R"N—CO—$R_1$ is selected from the group consisting of N,N-dimethylformamide, N,N-diethylformamide, N,N-di-n-propylformamide, N,N-dimethylacetamide, N,N-diethylacetamide, N,N-di-n-propylacetamide, N,N-dimethylpropionamide, N,N-diethylpropionamide and N,N-di-n-propylpropionamide.

9. The process for the preparation of 1-benzyl-3-hydroxymethyl-1H-indazole represented by formula (II) according to claim 1, in which the said stage b') is carried out using a molar ratio between the 1-benzyl-3-halogeno-1H-indazole of formula (III) and the amide of formula R'R"N—CO—$R_1$ of between 1 and 4.

10. The process for the preparation of 1-benzyl-3-hydroxymethyl-1 H-indazole represented by formula (II) according to claim 1, in which the said carbonyl group reducing agent used in stage b') is selected from the group consisting of $NaBH_4$, $KBH_4$, $LiBH_4$, $Zn(BH_4)_2$, $Ca(BH_4)_2$, $NaAlH_4$, $LiAlH_4$, $Et_3SiH$, $Bu_3SnH$, i-$Bu_2AlH$, 70% $NaAlH_2(OCH_2CH_2OCH_3)_2$ in toluene, preferably 70% $NaAlH_2(OCH_2CH_2OCH_3)_2$ in toluene.

11. The process for the preparation of 1-benzyl-3-hydroxymethyl-1H-indazole represented by formula (II) according to claim 1, in which the $R_1$-$R_8$ groups in the formulae (II), (III), (IV) and (VIII) described previously may have the following meanings:

$R_1$ and $R_2$, which may be the same or different, are represented by a hydrogen atom, or an alkyl group having 1 to 3 carbon atoms, $R_3$, $R_4$ and $R_8$, which may be the same or different, may be hydrogen, a methyl group, an ethyl group, a methoxy group, an ethoxy group, a chlorine atom and a fluorine atom, $R_5$ may be hydrogen, a methyl group, an ethyl group, a methoxy group, an ethoxy group, a chlorine atom and a fluorine atom, or together with $R_6$ and $R_7$ may form a ring having 6 carbon atoms, and $R_6$ and $R_7$, which may be the same or different, may be hydrogen, a methyl group, an ethyl group, or one of $R_6$ and $R_7$ together with $R_5$ may form a ring having 6 carbon atoms.

12. An intermediate compound represented by the following formula (IV):

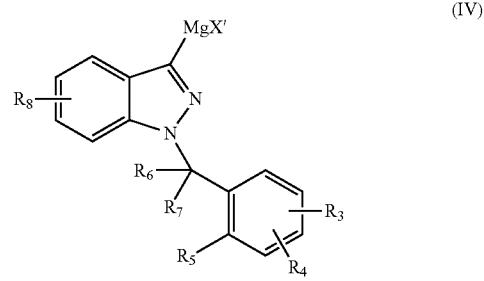

in which

X' is a halogen atom selected from bromine and chlorine, $R_3$, $R_4$ and $R_8$, which may be the same or different, may be hydrogen, an alkyl group having 1 to 5 carbon atoms, an alkoxy group having 1 to 3 carbon atoms, and a halogen atom, $R_5$ may be hydrogen, an alkyl group having 1 to 5 carbon atoms, an alkoxy group having 1 to 3 carbon atoms, a halogen atom, or together with one of $R_6$ and $R_7$ may form a ring having 5 or 6 carbon atoms, and $R_6$ and $R_7$, which may be the same or different, may be hydrogen, an alkyl group having 1 to 5 carbon atoms, or one of $R_6$ and $R_7$ together with $R_5$ may form a ring having 5 or 6 carbon atoms.

13. The intermediate compound represented by formula (IV) according to claim 12 in which X' is a chlorine atom, $R_3$, $R_4$ and $R_8$, which may be the same or different, may be hydrogen, a methyl group, an ethyl group, a methoxy group, an ethoxy group, a chlorine atom and a fluorine atom, $R_5$ may be hydrogen, a methyl group, an ethyl group, a methoxy group, an ethoxy group, a chlorine atom and a fluorine atom, or together with one of $R_6$ and $R_7$ may form a ring having 6 carbon atoms, $R_6$ and $R_7$, which may be the same or different, may be hydrogen, a methyl group, an ethyl group, or one of $R_6$ and $R_7$ together with $R_5$ may form a ring having 6 carbon atoms.

14. The process for the preparation of 1-benzyl-3-hydroxymethyl-1H-indazole represented by formula (II) according to claim 1, in which X is iodine.

15. The process for the preparation of 1-benzyl-3-hydroxymethyl-1H-indazole represented by formula (II) according to claim 1, in which X' is chlorine.

16. The process for the preparation of 1-benzyl-3-hydroxymethyl-1H-indazole represented by formula (II) according to claim 1, in which the said stage a) is carried out using a molar ratio between the alkyl magnesium halide of formula RMgX' and the 1-benzyl-3-halogeno-1H-indazole of formula (III) of between 1.5 and 4.

17. The process for the preparation of 1-benzyl-3-hydroxymethyl-1H-indazole represented by formula (II) according to claim 1, in which the said amide of formula R'R"N—CO—$R_1$ is N,N-dimethylformamide.

18. The process for the preparation of 1-benzyl-3-hydroxymethyl-1H-indazole represented by formula (II) according to claim 1, in which the said carbonyl group reducing agent used in stage b') is 70% $NaAlH_2(OCH_2CH_2OCH_3)_2$ in toluene.

19. The process for the preparation of 1-benzyl-3-hydroxymethyl-1H-indazole represented by formula (II) according to claim 1, in which the said alkyl magnesium halide of formula RMgX' is i-propylMgCl.

20. The process for the preparation of 1-benzyl-3-hydroxymethyl-1H-indazole represented by formula (II) according to claim 1, in which the said carbonyl compound of formula $R_1$—CO—$R_2$ is formaldehyde.

* * * * *